Figure 1:
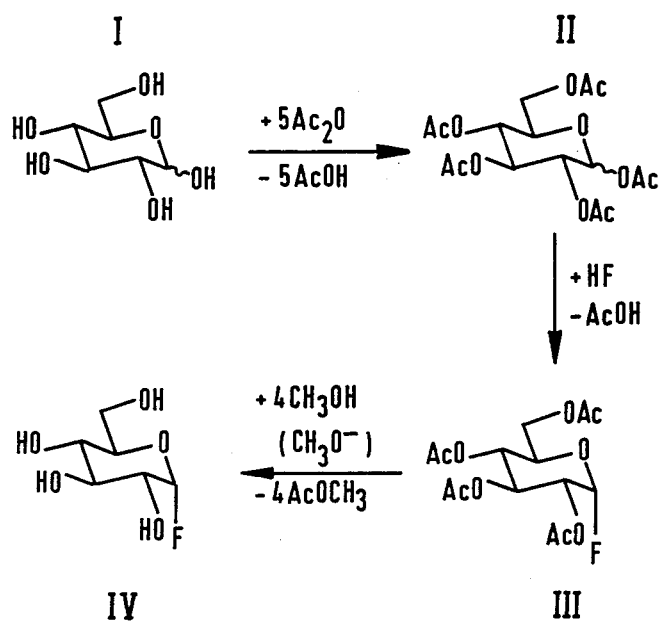
Figure 1:
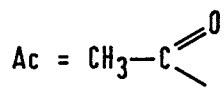

United States Patent [19]

Franz et al.

[11] Patent Number: 4,847,372

[45] Date of Patent: Jul. 11, 1989

[54] PROCESS FOR THE SINGLE-STAGE PREPARATION OF GLYCOSYL FLUORIDES

[75] Inventors: Raimund Franz, Kelkheim; Hans M. Deger, Hofheim am Taunus; Merten Schlingmann, Königstein, all of Fed. Rep. of Germany

[73] Assignee: Hoechst Aktiengesellschaft, Frankfurt am Main, Fed. Rep. of Germany

[21] Appl. No.: 45,752

[22] Filed: Apr. 28, 1987

Related U.S. Application Data

[63] Continuation of Ser. No. 771,674, Sep. 3, 1905, abandoned.

[30] Foreign Application Priority Data

Sep. 5, 1984 [DE] Fed. Rep. of Germany ....... 3432565

[51] Int. Cl.$^4$ ............................................. C07H 1/00
[52] U.S. Cl. ..................................... 536/127; 536/11; 536/4.1; 536/122; 536/124
[58] Field of Search ................ 536/1.1, 124, 127, 122, 536/4.1

[56] References Cited

U.S. PATENT DOCUMENTS

4,233,277 11/1980 Sheppard ........................... 423/297

FOREIGN PATENT DOCUMENTS

2104063 3/1983 United Kingdom ................ 536/122

OTHER PUBLICATIONS

Brauns, Fluoro-Acetyl Derivatives of Sugars, Journal of American Chemical Society, vol. 45, 833 (1923).
D. T. A. Lamport et al., Biotechnology and Bioengineering, vol. XXIV (1982).
Defaye, Gadelle and Pederson, Carbohydrate Research, 110 (1982).
B. Helferich et al., Liebigs Annalen der Chemie, 1926, p. 447.
Chemical Abstracts, vol. 101, 171601e.
Chemical Abstracts, vol. 102, 8411e.
Migrdichian, *Organic Synthesis,* vol. 1, 1957, p. 52.

*Primary Examiner*—Johnnie R. Brown
*Assistant Examiner*—Elli Peselev
*Attorney, Agent, or Firm*—Finnegan, Henderson, Farabow, Garrett & Dunner

[57] ABSTRACT

A process for the single-stage preparation of glycosyl fluorides by dissolving saccharides in liquid hydrogen fluoride and evaporating the hydrogen fluoride, wherein the resulting glycosyl fluoride is isolated in such a way that, when the evaporation of the hydrogen fluoride is started at a relatively high temperature, in general at $-20°$ to $+20°$ C., the evaporation is effected at a high evaporation rate or, when a low evaporation rate is used at the start of the evaporation, a sufficiently low temperature is set, in general $-80°$ C. to $-30°$ C.

15 Claims, 2 Drawing Sheets

PROCESS FOR THE SINGLE-STAGE PREPARATION OF GLYCOSYL FLUORIDES

This application is a continuation, of application Ser. No. 771,674, filed Sept. 3, 1985, now abandoned.

Due to their relative stability and particular reactivity, the fluorine compounds are in a special position amongst the 1-halogeno-sugars (glycosyl halides). This applies in particular to glycoside syntheses which are carried out with glycosyl halides. Glycosyl fluorides are the only a-halogeno-sugars which are stable without protection of the remaining hydroxyl groups, but the stabilties of the anomeric forms can differ. Thus, for example, α-glucosyl fluoride is more stable than the β-form.

Even though the glycosyl fluorides without protective groups are stable, as mentioned, the literature method for their preparation is relatively involved and proceeds in three stages, starting from pure carbonhydrate (monosaccharide). The present invention now relates to a method for the single-stage preparation of 1-fluorosugars (glycosyl fluorides) from a carbonhydrate.

The state of the art may be illustrated by taking the preparation of α-glucosyl fluoride as an example. In this case, the method of B. Helferich et al. (Liebigs Annalen der Chemie 447 (1926), page 27 et seq.) is still used, according to which glucose (I) must be converted in stage 1 into its pentaacetate (II). Only the latter can be converted in stage 2 by means of liquid hydrogen fluoride into tetraacetyl-α-glucosyl fluoride (III) which, finally, must be converted in stage 3 in a kind of transesterification with methanol in the presence of methylate into the α-glucosyl fluoride (IV) free of protective groups (see the formula diagram in FIG. 1).

An additional serious disadvantage is that the hydrogen fluoride used in the fluorination (stage 2) is lost, and partial deacetylation, which must be overcome by reacetylation if necessary, can occur and that the eliminatin of the protective groups by methylate can also cause a dehydrofluorination with the formation of a sugar anhydride, whereby the purity of the end product can be impaired and lead to disadvantages in subsequent reactions.

Figure 2:
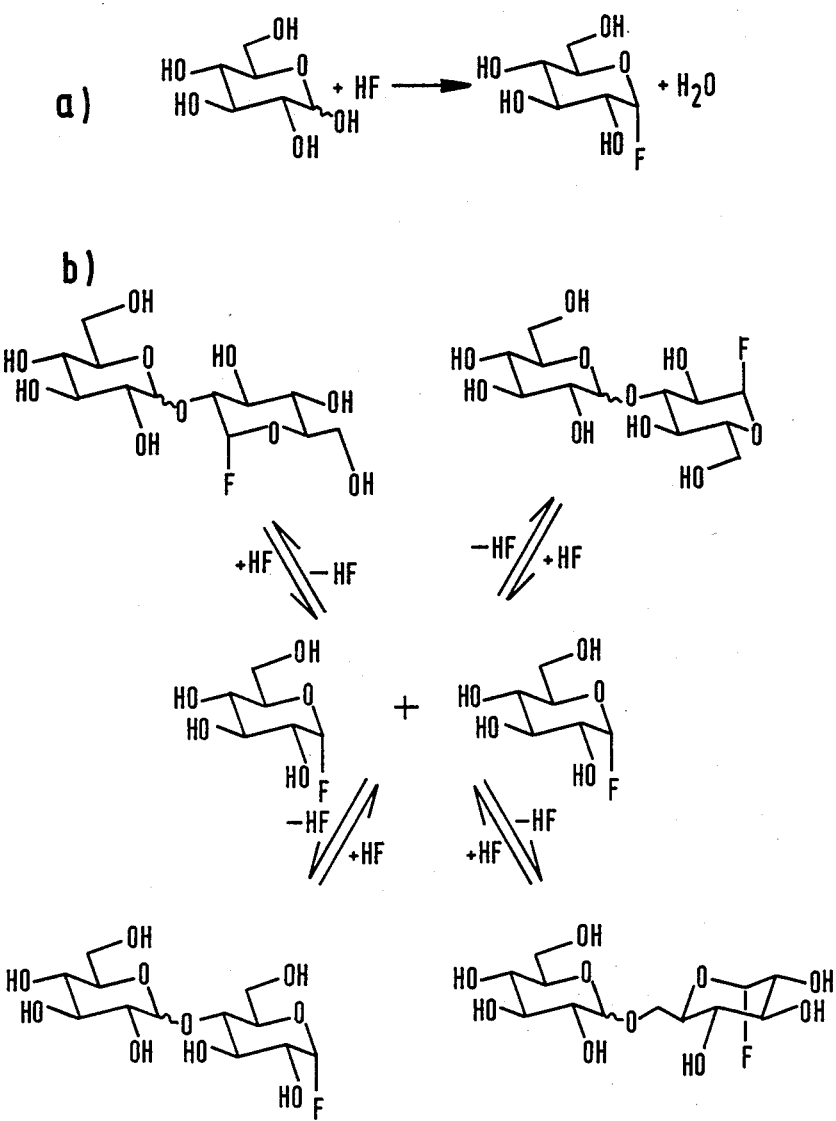

The relative stability of the glycosyl fluorides, for example of α-glucosyl fluoride, suggests the idea of preparing this product in one stage directly from the monosaccharide, for example glucose, and hydrogen fluoride. It is in fact known that monosaccharides, and also oligoand poly-saccharides such as starch of cellulose, readily react with hydrogen fluoride, forming glycosyl fluorides (cf. Defaye, Gadelle and Pedersen, Carbohydrate Research 110 (1982), pages 217–227, with further literature references, see the formula diagram in FIG. 2a). As can also be found in this literature reference, however, the glucosyl fluoride formed is in a concentration-dependent equilibrium with reversion products, i.e. products of a reaction of the glycosyl fluoride with any hydroxyl group of a neighboring molecule, in accordance with the formula diagram in FIG. 2b. The fluorinated disaccharides thus formed can likewise condense, in equilibrium, with further monosaccharide, oligosaccharide or polymer saccharide molecules in the reaaction mixture. As this literature reference also shows, the equilibrium is shifted in the direction of the oligosaccharides (reversion products) during the evaporation of the hydrogen fluoride.

In order to avoid the undesired, concentration-dependent shift of the equilibria towards the reversion products, glucosyl fluoride has also been isolated in the past from a dilute solution in hydrogen fluoride by precipitation with diethyl ether (Defaye, Gadelle and Pedersen, loc. cit.). For safety reasons, however, this method is unsuitable for relatively large quantities (risk of fire and explosion in connection with diethyl ether); moreover, the loss of hydrogen fluoride and diethyl ether must be accepted, since they are difficult to separate from one another, so that this method is very expensive and can be used only for scientific purposes. Another known method which, however, is similarly impracticable for large quantities, is the direct neutralizaiton of the solution of glucosyl fluoride with calcium carbonate (H. Hardt et al., Biotechnology and Bioengineering, Volume XXIV, pages 903–918 (1982)). Moreover, this process gives yields of less than 20%.

It was therefore the object to develop a process which permits recovery of the hydrogen fluoride, does not require a precipitating agent and nevertheless proceeds without reversion of the initially formed glycosyl fluoride.

It has now been found, surprisingly, that the rate at which the said concentration-dependent reversion equilibrium is established depends very sharply on the temperature, so that a reversion can simply be avoided by selecting a suitably low evaporation temperature and/or a suitable high evaporation rate for the working-up of a solution of a glycosyl fluoride in hydrogen fluoride.

The present invention thus relates to a process for the single-stage preparation of glycosyl fluorides by dissolving saccharides, ie. monosaccharides, oligosaccharides or polysaccharides, in liquid hydrogen fluoride and evaporating the hydrogen fluoride, which process comprises isolating the resulting glycosyl fluoride in such a way that, when the evaporation is started at a relatively high temperature, the evaporation is effected at a high evaporation rate or, when a low evaporation rate is used at the start of the evaporation, a sufficiently low temperature is set.

In other words, the invention also concerns a process for separating off the excess hydrogen fluoride from the reaction mixture of saccharides and liquid hydrogen fluoride, with isolation of the glycosyl fluorides, which process comprises evaporating the excess hydrogen fluoride in such a way that, in the case of a relatively high temperature at the start of the evaporation, a high evaporation rate if effected or, when a low evaporation rate is used at the start of the evaporation, a sufficiently low temperature is set.

In the process according to the invention, the glycosyl fluoride is naturally obtained in the thermodynamically more stable stereomeric form, usually in the α-form.

The temperature at the start of evaporation can be at any point within the entire liquid range of the solution of the starting material in hydrogen fluoride between −80° C. and the boiling point of hydrogen fluoride under atmospheric pressure, which is +20° C. under normal pressure. A preferred range, however, is that beween −50° C. and 0° C., in particular that between −40° C. and −20° C., higher tempertues up to the upper limits of the indicated ranges being permissible at higher evaporation rates and lower temperatues being advantageously maintained at lower evaporation rates, ie. these temperatures are then set in the vicinity of the lower limits of the indicated ranges.

The term "relatively high temperature at the start of evaporation" is to be understood as meaning temperatures in the range from −20 to +20, preferably from −20° to 0° C., and the term "low temperature at the start of evaporation" is to be understood as meaning a temperature in the range from −80 to −30, preferably from −50° to −30° C. Since the invention endeavors to avoid the reversion of glycosyl fluoride, it is of course also preferred, in the range from −50° to 0° C., or in the narrower preferred range between −40° and −20° C., to take those measures which act against reversion,ie. to effect the highest possible evaporation rate. A low temperature at the start of evaporation can be set, for example, by a distillation under reduced pressure, or by evaporation of the hydrogen fluoride by blowing in an inert gas (for example air, nitrogen, carbon dioxide or rare gases) without or preferably with external cooling. It is also possible, however, by generating such a high evaporation rate and hence a high consumption of latent heat of evaporation per unit time, to effect such intensive internal cooling of the solution that external cooling is unnecessary.

The high evaporation rate necessary particularly in the latter case can be generated, for example, by applying conventional processes, such as mechanical atmomization or spray-drying, or thin-layer or falling-film evaporation. In these cases, the evaporation residue is advantageously neutralized immediately, preferably continuously, or deep-forzen before further processing, for example by means of solid carbon dioxide.

Hydrogen fluoride and saccharides are normally miscible in any proportions. In the solutions subjected to the treatment according to the invention the hydrogen fluoride/saccharide ratio can, for example, be at least 4. In general, however, it is at least 7 and in particular at least 9. Theorectically, the ratio can be very large, for example 100, but this is of course not practicable for reasons of industrial handling, so that in general the excess of hydrogen fluoride is restricted in an industrially sensible manner, for eample to at most a 20-fold or 30-fold excess.

The starting materials used for the preparation of glycosyl fluorides according to the inventtion can be the monomeric aldo- and keto-tetroses, -pentoses, -hexoses, -heptoses, -octoses and -nonoses, and also glycosidically lniked oligo- and poly-saccharides, the glycosidic bonds of which can be cleaved by means of hydrogen fluoride. The following are mentioned as examples of monosaccharides which can be used in this way: glucose, galactose, mannose, allose, fructose, sorbose, fucose, rhamnose, xylose, ribose, arabinose and erythrose. The following are listed as examples of glycosidicallylinked oligo- and poly-saccharides: maltose, isomaltose, cellobiose,lactose, sucrose, raffinose, cellodextrin, amylose, amylopectin and cellulose, it being self-evident that only a starting material of uniform structure can serve for the preparation of a glycosyl fluoride of uniform composition.

The materials used for the reaction vessel or the evaporation apparatus can be any materials which are resistant to hydrogen fluoride under the reaction conditions, such as polyethylene, polypropylene, copolymers of hexafluoropropene and vinylidene fluoride, for example ®Viton, polytetafluoroethylene, polytrifluorochloroethylene, chrome-nickel steel, pure nickel, Monel metal, silver, gold and platinum. Unalloyed steel can also be used as a metallic material for those parts of the apparatus which are less severely stressed.

The chosen starting material is dissolved in hydrogen fluoride in the conventional manner with stirring; advantageously, the hydrogen fluoride is introduced first and the solid saccharide is metered in. The heat of reaction and solvation, thus liberated can be removed, for example, by external cooling or reflux cooling or can be consumed as latent heat of evaporation.

After the saccharide employed as the starting material has dissolved, it is advantageous to complete the reaction over some further period, for example about 15 to 200 minutes, preferbly 30 to 100 minutes, if appropriate with stirring, preferably within the temperature range amount used, depending on the evaporation method applied. from 0° to 20° C. According to the invention, the clear reaction solution is then subjected to the evaporation process.

The hydrogen fluoride evaporated in the process according to the invention can as a rule be re-used directly, after condensation in a suitable condenser. The yield of recovered hydrogen fluoride can far exceed 90% of the amount used, depending on the evaporation method applied.

The evaporation residue which may have been cooled and contains the crude glycosyl fluoride, residual quantities of hydrogen fluoride and sometimes water of reaction, can in turn be neutralized in the conventional manner, for example by means of calcium carbonate in aqueous suspension (cf. H. Hardt et al.,loc, cit.). The isolation of the 1-fluoro-sugar from the neutral aqueous filtrate can be effected, for example, by evaporation. However, gentle methods such as freeze-drying are preferred. Since losses can occur only in connection with a single filtration step, the yields are always very high, and as a rule almost quantitative. The product thus obtained is in most cases sufficiently pure for further use. Since the stabilities of the gylcosyl fluorides differ somewhat, the corresponding fluorine-free monosaccharide, for example galactose, sometimes appears as an impurity in small quantities, for example up to 5%. Apart from elemental analysis, especially the thin-layer chromatogram is suitable for identification and purity control.

Compared with the state of the art, the process according to the invention has the following two great advantages:

(a) It is a single-stage reaction starting from a carbohydrate which is unprotected on the hydroxyl groups and can be not only a monosaccharide but also an inexpensive polymeric saccharide, namely an oligosaccharide or polysaccharide, such as starch or cellulose; at the same time, the polymeric saccharides are degraded to monomeric of oligomeric products.

(b) Almost all the relatively expensive hydrogen fluoride can be recovered and re-used.

The two advantages have the effect that glycosyl fluorides can be prepared more rapidly, more simply and more cheaply than hitherto by the procedure according to the invention. The examples which follow are intended to illustrate the process in more detail.

EXAMPLE 1

In a semi-transparent, closable vessel of polyethylene, fitted with a magnetic stirrer device and thermometer, 50 g of hydrogen fluoride were introduced and cooled by means of a dry ice bath to −50° C.; the cooling bath was then removed. While blanketing with dry nitrogen, 5 g of glucose were then introduced with stirring at such a rate that the end temperature reached about +5°

C. The clear, only slightly colored reaction solution thus obtained was left to stand sealed for 1 hour at room temperature, with occasional stirring, and then cooled to −30° C. A dry nitrogen stream was then passed by means of a gas inlet tube of polyethylene at a rate of about 100 liters per hour into the solution, and during this time the temperature of the external cooling bath was regulated such that an internal temperature of about −30° C. was maintained. The gas stream was passed into a condenser charged with dry ice, wherein the hydrogen fluoride condensed and could be collected in a cooled receiver. After 1.5 hours, the now viscous sirup was mixed under pH control with an aqueous suspension of finely powdered calcium carbonate. Finally, a few drops of saturated aqueous calcium hydroxide solution were added to the reaction product until the pH remained constant at 7.5, and the liquid was filtered with suction. The clear filtrate was freeze-dried and gave 4.6 g of crude glucosyl fluoride.

Analysis:

The melting range was 115°–118° C. (decomposition) in good agreement with the literature; there was no depression on mixing with authentic material.

Elemental analysis:

Fluorine found 10.5%; calculated 10.4% Thin-Layer chromatography on silica gel G, solvent ethyl acetate/isopropanol/water (23:65:12): no difference when compared with authentic material.

$^1$H, $^{19}$F and $^{13}$C nuclear magnetic resonance spectroscopy confirms the presence of the α-anomer.

EXAMPLE 2

In a distillation flask of polytetrafluoroethylene, a solution of 10 g of glucose in 100 g of hydrogen fluoride, prepared analogously to Example 1, was distilled under reduced pressure at an internal temperature of −30° C. The pressure was regulated between 100 and 130 mbar in such a way that steady distillation took place. After 2.5 hours, the residual HF content in the bottoms from the distillation was then only 5 g. The distillation was terminated, and the residue worked up in accordance with Example 1. 9.5 g of glucosyl fluoride were obtained.

EXAMPLE 3

In an apparatus and by the procedure according to Example 1, 1 g of D-galactose was reacted with 10 g of hydrogen fluoride, the mixture was left to stand for 1 hour at −30° to −40° C. and the hydrogen fluoride was then stripped out within 15 minutes by blowing in nitrogen. The working-up gave α-D-galactosyl fluoride (about 1 g) which was identified by elemental analysis, thin-layer chromatogram and $^{19}$F and $^{13}$C nuclear magnetic resonance spectra (cf. J. E. C. Barnett et al., Biochem. J. 105 (1967), page 669). Melting point: 130° (decomposition).

EXAMPLE 4

In the same way as described in Example 3, 1 g of D-mannose was reacted with 10 g of hydrogen fluoride. About 1 g of α-D-mannosyl fluoride ws isolated and identified by comparison with authentic material (cf. Barnett 35 al., loc. cit. in Example 3).

EXAMPLE 5

In an apparatus and by the procedure according to Example 1, 5 g of starch were reacted with 50 g of hydrogen fluoride. After a residence time of 1 hour at −30° to −35° C., the hydrogen fluoride ws stripped out by blowing within one hour. After this, the residual hydrogen fluoride content in the evaporation residue ws still 5 g. Neutralization with calcium carbonate as described and filtration using cellulose powder as a filter aid led to freezedried α-glucosyl fluoride.—Yield 4.2 g.

EXAMPLE 6

In an apparatus and by the procedure according to Example 1, 5 g of cellulose werre reacted with 50 g of hydrogen fluoride. The hydrogen fluoride ws stripped out at −30° C. by blowing within 1.5 hours. The residual HF content in the evaporation residue then was still 5 g. Neutralizaiton with calcium carbonate as described, filtration and freeze-drying gave α-glucosyl fluoride in a yield of 4.5 g.

EXAMPLE 7

In an apparatus and by the procedure according to Example 1, 5 g of D-glucose were reacted with 50 g of hydrogen fluoride. After the end of the further stirring period, the clear solution was transferred into a dropping funnel of polytrifluorochloroethylene and introduced dropwise from there into a cylindrical chamber of semi-transparent polyethylene, in which a fast-rotating blade stirrer ensured fine atomization of the solution. The escaping hydrogen fluoride was carried out of the chamber by means of an upward-directed nitrogen stream (300 liters/hour) and condensed in a condenser. Slight external heating by means of warm water at 40° C. on the wall of the chamber ensured rapid evaporation of the hydrogen fluoride from the sirup film running off. The sirupy evaporation residue ran continuously from the cooled bottom of the chamber into a receiver cooled with dry ice. The duration of evaporation was 15 minutes. The evaporation residue still contained 10 g of hydrogen fluoride and was worked up as described in Example 1. The yield of α-glucosyl fluoride was 4.6 g.

We claim:

1. In a process for manufacturing glycosyl fluoride wherein a saccharide that is unprotected on the hydroxyl groups is dissovled in liquid hydrogen fluoride to form glycosyl fluoride, the improvement comprising the isolation of glycosyl fluoride in one stage by:

vaporizing the hydrogen fluoride the temperature at the beginning of the vaporization being in the range of −80° to +20° C., in a manner such that, at a relatively high temperature within said range at the beginning, vaporization is carried out at a high rate and that, when operating with a low vaporization rate, a satisfactory low temperature within said range is applied at the beginning of the vaporization.

2. A process according to claim 1, wherein the temperature is in the range from −50° to 0° C.

3. A process according to claim 2, wherein the temperature is in the range from −40° to −20° C.

4. A process according to claim 1, wherein the relatively high temperature at the beginning of the vaporization is in the range from −20° to +20° C.

5. A process according to claim 4, wherein the temperature is in the range from −20° to 0° C.

6. A process according to claim 1, wherein the low temperature at the beginning of the vaporization is in the range from −80° to −30° C.

7. A process according to claim 6, wherein the temperature is in the range from −50° to −30° C.

8. A process according to claim 1, wherein at the beginning of the vaporization a low temperature is adjusted by distillation under reduced pressure or by blowing in an inert gas.

9. A process according to claim 1, wherein a high rate of vaporization is effected by mechanical spraying, spray drying, thin layer vaporization or falling film vaporization.

10. A process according to claim 1, wherein in the solution which is subjected to the vaporization the weight ratio between hydrogen fluoride and the starting saccharide ranges from at least 4:1 to at most 100:1.

11. A process according to claim 10 wherein in the weight ratio is at least 7:1 and at most 30:1.

12. A process according to claim 11, wherein the weight ratio is at least 9:1 and at most 20:1.

13. A process according to claim 1, wherein the glycosyl fluoride is a monomer conversion product produced under degradation from a polymer saccharide.

14. A process according to claim 13, wherein the glycosyl fluoride is a monomer conversion product produced under degradation from a polysaccharide.

15. A process according to claim 1, wherein the reaction is carried out in a device the portions of which are in contact with hydrogen fluoride consist of a material resistant to hydrogen fluoride.

* * * * *